(12) United States Patent
Keränen

(10) Patent No.: US 11,241,314 B2
(45) Date of Patent: Feb. 8, 2022

(54) DEVICE AND METHOD FOR IMPROVING THE FUNCTION OF A HEART VALVE

(71) Applicant: Medtentia International Ltd. Oy, Espoo (FI)

(72) Inventor: Olli Keränen, Bjärred (SE)

(73) Assignee: Medtentia International Ltd Oy, Espoo (FI)

( * ) Notice: Subject to any disclaimer, the term of this patent is extended or adjusted under 35 U.S.C. 154(b) by 0 days.

(21) Appl. No.: 16/253,153

(22) Filed: Jan. 21, 2019

(65) Prior Publication Data

US 2019/0151087 A1 May 23, 2019

Related U.S. Application Data

(60) Continuation of application No. 14/818,163, filed on Aug. 4, 2015, now Pat. No. 10,195,029, which is a
(Continued)

(30) Foreign Application Priority Data

Sep. 7, 2005 (SE) ..................... 0501993-0

(51) Int. Cl.
*A61F 2/24* (2006.01)

(52) U.S. Cl.
CPC .......... *A61F 2/2445* (2013.01); *A61F 2/2442* (2013.01); *A61F 2210/0004* (2013.01);
(Continued)

(58) Field of Classification Search
CPC ............ A61F 2/2409; A61F 2220/0008; A61F 2250/0067; A61F 2/2418;
(Continued)

(56) References Cited

U.S. PATENT DOCUMENTS 3,656,185 A 4/1972 Carpentier
3,997,923 A 12/1976 Possis
(Continued)

FOREIGN PATENT DOCUMENTS

DE 1960542 A1 1/1998
WO WO1995/016407 A1 6/1995
(Continued)

OTHER PUBLICATIONS

European Patent Office, Extended European Search Report dated Jun. 5, 2014 in European Patent Application No. 14164113.4, 7 pages.
(Continued)

*Primary Examiner* — Ann Schillinger
(74) *Attorney, Agent, or Firm* — Inskeep IP Group, Inc.

(57) ABSTRACT

A device for improving the function of a heart valve comprises: a support member formed from a shape memory material, and a restraining member providing a restraining action on a course of the support member. The support member may abut one side of the valve conforming to the shape of the valve annulus upon said shape memory material assuming an activated shape while the restraining member restrains the course of the support member. The restraining action is removable for allowing the support member to assume a desired, altered course. The restraining member may be biodegradable to be degraded within a patient or may be detachable from the support member to be withdrawn. The support member according to another embodiment presents a shape change in that an increased cross-section is associated with a shortened length of the support member. The support member according to yet another embodiment has a first and a second activated shape.

11 Claims, 11 Drawing Sheets

Related U.S. Application Data continuation of application No. 12/880,007, filed on Sep. 10, 2010, now Pat. No. 9,119,718, which is a division of application No. 12/065,884, filed as application No. PCT/SE2006/001019 on Sep. 5, 2006, now Pat. No. 8,128,691.

(52) U.S. Cl.
CPC ............... *A61F 2210/0014* (2013.01); *A61F 2210/0085* (2013.01); *A61F 2230/0065* (2013.01); *A61F 2230/0091* (2013.01); *A61F 2250/0003* (2013.01)

(58) Field of Classification Search
CPC ............ A61F 2002/9522; A61F 2/2412; A61F 2/2427; A61F 2/2445; A61F 2/2442; A61F 2210/0085; A61F 2230/0065; A61F 2250/0003; A61F 2210/0014; A61F 2230/0091; A61F 2210/0004
See application file for complete search history.

(56) References Cited

U.S. PATENT DOCUMENTS

| | | |
|---|---|---|
| 4,042,979 A | 8/1977 | Angell |
| 4,055,861 A | 11/1977 | Carpentier et al. |
| 4,489,446 A | 12/1984 | Reed |
| 4,535,483 A | 8/1985 | Klawitter et al. |
| 4,602,911 A | 7/1986 | Ahmadi et al. |
| 4,863,460 A | 9/1989 | Magladry |
| 4,917,698 A | 4/1990 | Carpentier et al. |
| 5,061,277 A | 10/1991 | Carpentier et al. |
| 5,062,829 A | 11/1991 | Pryor et al. |
| 5,104,407 A | 4/1992 | Lam et al. |
| 5,163,953 A | 11/1992 | Vince |
| 5,201,880 A | 4/1993 | Wright et al. |
| 5,290,300 A | 3/1994 | Cosgrove et al. |
| 5,306,296 A | 4/1994 | Wright et al. |
| 5,403,305 A | 4/1995 | Sauter et al. |
| 5,607,471 A | 3/1997 | Seguin et al. |
| 5,669,919 A | 9/1997 | Sanders et al. |
| 5,674,279 A | 10/1997 | Wright et al. |
| 5,716,397 A | 2/1998 | Myers |
| 5,776,189 A | 7/1998 | Khalid |
| 5,824,066 A | 10/1998 | Gross |
| 5,867,436 A | 3/1999 | Vanney et al. |
| 5,888,240 A | 3/1999 | Carpentier et al. |
| 5,908,450 A | 6/1999 | Gross et al. |
| 6,059,827 A | 5/2000 | Fenton, Jr. |
| 6,183,512 B1 | 2/2001 | Howanec, Jr. et al. |
| 6,207,610 B1 | 4/2001 | Carpentier et al. |
| 6,258,117 B1 | 7/2001 | Camrud et al. |
| 6,348,068 B1 | 2/2002 | Campbell et al. |
| 6,368,348 B1 | 4/2002 | Gabbay |
| 6,402,781 B1 | 6/2002 | Langberg et al. |
| 6,406,492 B1 | 6/2002 | Lytle |
| 6,406,493 B1 | 6/2002 | Tu et al. |
| 6,419,696 B1 | 7/2002 | Ortiz et al. |
| 6,458,153 B1 | 10/2002 | Bailey et al. |
| 6,585,767 B1 | 7/2003 | Holley et al. |
| 6,602,289 B1 | 8/2003 | Colvin et al. |
| 6,702,826 B2 | 3/2004 | Liddicoat et al. |
| 6,723,038 B1 | 4/2004 | Schroeder et al. |
| 6,730,121 B2 | 5/2004 | Ortiz et al. |
| 6,780,229 B2 | 9/2004 | Berreklouw |
| 6,964,684 B2 | 11/2005 | Ortiz et al. |
| 7,077,861 B2 | 7/2006 | Spence |
| 7,186,265 B2 | 3/2007 | Sharkawy et al. |
| 7,291,168 B2 | 11/2007 | Macoviak et al. |
| 2001/0021874 A1 | 9/2001 | Carpentier et al. |
| 2002/0013621 A1 | 1/2002 | Stobie et al. |
| 2002/0143381 A1 | 10/2002 | Gilligan et al. |
| 2002/0173841 A1 | 11/2002 | Ortiz et al. |
| 2003/0045929 A1 | 3/2003 | McCarthy et al. |
| 2003/0069593 A1* | 4/2003 | Tremulis ............... A61F 2/2445 606/142 |
| 2003/0176916 A1 | 9/2003 | Ryan et al. |
| 2003/0199975 A1 | 10/2003 | Gabbay |
| 2004/0019357 A1 | 1/2004 | Campbell et al. |
| 2004/0106989 A1 | 6/2004 | Wilson et al. |
| 2004/0127981 A1 | 7/2004 | Rahdert et al. |
| 2004/0127982 A1 | 7/2004 | Machold et al. |
| 2004/0138745 A1 | 7/2004 | Macoviak et al. |
| 2004/0143323 A1 | 7/2004 | Chawla |
| 2004/0148021 A1 | 7/2004 | Cartledge et al. |
| 2004/0162611 A1 | 8/2004 | Marquez |
| 2004/0167620 A1 | 8/2004 | Ortiz et al. |
| 2004/0220593 A1 | 11/2004 | Greenhalgh |
| 2004/0243230 A1 | 12/2004 | Navia et al. |
| 2004/0260393 A1 | 12/2004 | Rahdert et al. |
| 2005/0010275 A1 | 1/2005 | Sahatjian et al. |
| 2005/0010287 A1 | 1/2005 | Macoviak et al. |
| 2005/0107871 A1 | 5/2005 | Realyvasquez et al. |
| 2005/0119734 A1 | 6/2005 | Spence et al. |
| 2005/0137689 A1 | 6/2005 | Salahieh et al. |
| 2005/0149114 A1 | 7/2005 | Cartledge et al. |
| 2005/0149178 A1 | 7/2005 | Spence |
| 2005/0177228 A1 | 8/2005 | Solem et al. |
| 2005/0288777 A1 | 12/2005 | Rhee et al. |
| 2005/0288781 A1 | 12/2005 | Moaddeb et al. |
| 2006/0195134 A1 | 8/2006 | Crittenden |
| 2006/0195184 A1 | 8/2006 | Lane et al. |
| 2006/0195185 A1 | 8/2006 | Lane et al. |
| 2006/0282162 A1 | 12/2006 | Nguyen et al. |
| 2007/0179604 A1 | 8/2007 | Lane |
| 2010/0030014 A1 | 2/2010 | Ferrazzi |
| 2010/0076549 A1 | 3/2010 | Keidar et al. |

FOREIGN PATENT DOCUMENTS

| | | |
|---|---|---|
| WO | WO1999/004730 A1 | 2/1999 |
| WO | WO2001/050985 A1 | 7/2001 |
| WO | WO2002/003892 A1 | 1/2002 |
| WO | WO2002/049546 A2 | 6/2002 |
| WO | WO2003/028558 A2 | 4/2003 |
| WO | WO 2003/028592 A1 | 4/2003 |
| WO | WO2003/105730 A1 | 12/2003 |
| WO | WO 2004/019816 A2 | 3/2004 |
| WO | WO2004/030569 A2 | 4/2004 |
| WO | WO2004/071333 A2 | 8/2004 |
| WO | WO2004/089250 A1 | 10/2004 |
| WO | WO2006/012011 A2 | 2/2005 |
| WO | WO2005/039452 A1 | 5/2005 |
| WO | WO2005/112832 A1 | 12/2005 |
| WO | WO2005/122964 A1 | 12/2005 |
| WO | WO2006/054930 A1 | 5/2006 |
| WO | WO2006/065212 A1 | 6/2006 |
| WO | WO2006/091163 A1 | 8/2006 |
| WO | WO2006/093656 A1 | 9/2006 |
| WO | WO2007/030063 A1 | 3/2007 |
| WO | WO2007/138571 A2 | 12/2007 |
| WO | WO2008/058940 A1 | 5/2008 |

OTHER PUBLICATIONS

European Patent Office, Extended European Search Report dated Jun. 5, 2014 in European Patent Application No. 14164114.2, 6 pages.

WIPO, International Preliminary Examining Authority (European Patent Office), International Preliminary Report on Patentability dated Jan. 14, 2014 in International Patent Application No. PCT/EP2012/072272, 15 pages.

WIPO, International Preliminary Examining Authority (Euoprean Patent Office), International Preliminary Report on Patentability dated Sep. 24, 2013 in International Patent Application No. PCT/EP2012/072285, 9 pages.

WIPO, International Preliminary Examining Authority (European Patent Office), International Preliminary Report on Patentability dated Sep. 24, 2013 in International Patent Application No. PCT/EP2012-058278, 10 pages.

(56) References Cited

OTHER PUBLICATIONS

WIPO, European International Search Authority, International Search Report dated Aug. 19, 2013 in International Patent Application No. PCT/EP2013/051366, 7 pages.

WIPO, European International Search Authority, International Search Report dated Dec. 21, 2012 in International Patent Application No. PCT/EP2012/072285, 4 pages.

WIPO, European International Search Authority, International Search Report dated Dec. 21, 2012 in International Patent Application No. PCT/EP2012/072272, 4 pages.

WIPO, International Preliminary Examining Authority (European Patent Office), International Preliminary Report on Patentability dated Jun. 14, 2010 in International Patent Application No. PCT/EP2008-068126, 13 pages.

WIPO, International Preliminary Examining Authority (European Patent Office), International Preliminary Report on Patentability dated Apr. 22, 2010 in International Patent Application No. PCT/EP2008/068126, 13 pages.

WIPO, International Preliminary Examining Authority (European Patent Office), International Preliminary Report on Patentability dated Nov. 24, 2008 in International Patent Application No. PCT/EP2007/062225, 7 pages.

WIPO, International Preliminary Examining Authority (European Patent Office), International Preliminary Report on Patentability dated Mar. 11, 2008 in International Patent Application No. PCT/SE2006/001019, 12 pages.

WIPO, European International Search Authority, International Search Report and Written Opinion dated Feb. 29, 2008 in International Patent Application No. PCT/EP2007/062225, 11 pages.

WIPO, International Preliminary Examining Authority (European Patent Office), International Preliminary Report on Patentability dated Sep. 11, 2007 in International Patent Application No. PCT/SE2006/000251, 1 page.

WIPO, International Preliminary Examining Authority (European Patent Office), International Preliminary Report on Patentability dated Jun. 19, 2007 in International Patent Application No. PCT/SE2005/001914, 7 pages.

WIPO, European International Search Authority, Written Opinion dated Jan. 26, 2007 in International Patent Application No. PCT/SE2006/001019, 11 pages.

WIPO, European International Search Authority, International Search Report dated Jan. 26, 2007 in International Patent Application No. PCT/SE2006/001019, 8 pages.

WIPO, European International Search Authority, International Search Report dated Jun. 2, 2006 in International Patent Application No. PCT/SE2006/000251, 5 pages.

WIPO, European International Search Authority, Written Opinion dated Jun. 2, 2006 in International Patent Application No. PCT/SE2006/000251, 7 pages.

WIPO, European International Search Authority, International Search Report dated Apr. 4, 2006 in International Patent Application No. PCT/SE2005/001914, 1 page.

WIPO, European International Search Authority, International Search Report and Written Opinion dated Mar. 1, 2006 in International Patent Application No. PCT/SE2005/000909, 6 pages.

WIPO, European International Search Authority, International Search Report dated Sep. 7, 2005 in International Patent Application No. PCT/SE2005/000440, 4 pages.

\* cited by examiner

DEVICE AND METHOD FOR IMPROVING THE FUNCTION OF A HEART VALVE

RELATED APPLICATIONS

The present application is a continuation of U.S. patent application Ser. No. 14/818,163 filed Aug. 4, 2015 entitled Device And Method For Improving The Function Of A Heart Valve, which is a continuation of U.S. patent application Ser. No. 12/880,007 filed Sep. 10, 2010 entitled A Device And Method For Improving The Function Of A Heart Valve, now U.S. Pat. No. 9,119,718 issued Sep. 1, 2015, which is a divisional of U.S. patent application Ser. No. 12/065,884 filed Sep. 3, 2008 entitled A Device And Method For Improving The Function Of A Heart Valve, now U.S. Pat. No. 8,128,691 issued Mar. 6, 2012, which claims priority to International Patent Application No. PCT/SE2006/001019 filed Sep. 5, 2006 entitled A Device And Method For Improving The Function Of A Heart Valve, which in turns claims priority to Swedish Patent Application No. 0501993-0 filed Sep. 7, 2005 entitled A Device And Method For Improving The Function Of A Heart Valve, all of which are hereby incorporated by reference.

FIELD OF THE INVENTION

The present invention generally relates to heart valve repair and annuloplasty devices. More specifically, the invention relates to the repair of heart valves having various malformations and dysfunctions.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak (insufficiency). The leaflets and chords may become calcified and thickened rendering them stenotic (obstructing forward flow). Finally, the valve relies on insertion of the chordae inside the ventricle. If the ventricle changes in shape, the valve support may become nonfunctional and the valve may leak.

Mitral and tricuspid valve replacement and repair are traditionally performed with a suture technique. During valve replacement, sutures are spaced around the annulus (the point where the valve leaflet attaches to the heart) and then the sutures are attached to a prosthetic valve. The valve is lowered into position and when the sutures are tied, the valve is fastened to the annulus. The surgeon may remove all or part of the valve leaflets before inserting the prosthetic valve. In valve repair, a diseased valve is left in situ and surgical procedures are performed to restore its function. Frequently an annuloplasty ring is used to reduce the size of the annulus. The ring serves to reduce the diameter of the annulus and allow the leaflets to oppose each other normally. Sutures are used to attach a prosthetic ring to the annulus and to assist in plicating the annulus.

In general, the annuloplasty rings and replacement valves must be sutured to the valve annulus and this is time consuming and tedious. If the ring is severely malpositioned, then the stitches must be removed and the ring repositioned relative to the valve annulus during restitching. In other cases, a less than optimum annuloplasty may be tolerated by the surgeon rather than lengthening the time of the surgery to restitch the ring.

During heart surgery, a premium is placed on reducing the amount of time used to replace and repair valves as the heart is frequently arrested and without perfusion. It would therefore be very useful to have a method to efficiently attach a prosthesis into the mitral or tricuspid valve position.

In U.S. Pat. No. 6,419,696, an annuloplasty device is disclosed. The device comprises a first and a second support ring configured to abut opposite sides of the valve annulus to thereby trap valve tissue therebetween. The device may be used in those situations that have conventionally utilized annuloplasty rings, but the device may be applied in a much easier manner by rotating the rings into position on opposite sides of the valve annulus.

OBJECTS AND SUMMARY OF THE INVENTION

It is an object of the invention to provide a more reliable and more easily accomplished valve repair. It is a specific object of the invention to facilitate insertion of an annuloplasty implant.

These and other objects of the invention are accomplished by means of a device and a method according to the independent claims. Preferred embodiments of the invention are apparent from the dependent claims.

Thus, according to a first aspect of the invention, there is provided a device for improving the function of a heart valve comprised of valve tissue including an annulus and a plurality of leaflets for allowing and preventing blood flow. The device comprises a support member at least partially formed from a shape memory material operable to assume an activated shape and an inactivated shape and a restraining member, which is arranged to provide a restraining action on a course of the support member. The support member is configured to abut one side of the valve and is arranged to conform to the shape of at least a part of the valve annulus upon said shape memory material assuming said activated shape while the restraining member exerts the restraining action on the course of the support member. The restraining member is formed of a biodegradable material to be degraded when the device is implanted in a patient, wherein degradation of the restraining member removes the restraining action and allows the support member to assume a desired, altered course.

According to a second aspect of the invention, there is provided a device for improving the function of a heart valve comprised of valve tissue including an annulus and a plurality of leaflets for allowing and preventing blood flow. The device comprises a support member being configured to abut one side of the valve and being arranged to conform to the shape of at least a part of the valve annulus. The support member has an inherent adaptation to a shape change such that an increased cross-section of at least part of the support member is associated with a shortened length of the support member, whereby the support member is susceptible to an expansion of a cross-section of the support member when the support member has conformed to the shape of at least part of the valve annulus such that the support member assumes a desired, altered shape.

According to a third aspect of the invention, there is provided a device for improving the function of a heart valve comprised of valve tissue including an annulus and a plurality of leaflets for allowing and preventing blood flow. The device comprises a support member at least partially formed from a shape memory material operable to assume a first activated shape, a second activated shape and an inactivated shape. The support member is configured to abut one side of the valve and is arranged to conform to the shape of at least a part of the valve annulus upon said shape memory material assuming said first activated shape. The support member is further configured to assume a desired, altered course for remodelling the valve annulus upon said shape memory material assuming said second activated shape. The shape memory material is arranged such that heating the shape memory material to a first temperature will bring the shape memory material to assume said first activated shape and further heating of the shape memory material to a second temperature will bring the shape memory material to assume said second activated shape.

According to a fourth aspect of the invention, there is provided a device for improving the function of a heart valve comprised of valve tissue including an annulus and a plurality of leaflets for allowing and preventing blood flow. The device comprises a support member at least partially formed from a shape memory material operable to assume an activated shape and an inactivated shape and a restraining member, which is arranged to provide a restraining action on a course of the support member. The support member is configured to abut one side of the valve and is arranged to conform to the shape of at least a part of the valve annulus upon said shape memory material assuming said activated shape while the restraining member exerts the restraining action on the course of the support member. The restraining member is detachable from the support member for releasing the restrain and allowing the support member to assume a desired, altered course.

According to all four aspects of the invention, the support member may be arranged in a configuration to abut one side of the valve conforming to the shape of at least a part of the valve annulus. The support member may also assume a desired, altered shape. According to all four aspects of the invention, the device provides a possibility of controlling when the support member is to assume the desired, altered shape. This implies that the support member may be fixed to the valve before assuming the desired, altered shape. Thus, all four aspects of the invention provide a possibility to control when the support member assumes the desired, altered shape.

According to the first and fourth aspects of the invention, the restraining member delays the support member from assuming the memorized, desired shape. The restraining member allows the support member to conforming to the shape of at least a part of the valve annulus, but it prevents the support member from assuming the desired course. This implies that the support member may be firmly anchored to the valve tissue before the support member assumes the desired course. Thus, when the restraining action is removed to release the restrain on the support member, the support member will bring the valve tissue with it in assuming the desired course. The shape change of the support member may be designed such that valve tissue is drawn towards the opening in the valve in order for the valve to be remodelled for allowing the valve leaflets to close properly.

The support member may have an initial shape, when inserted to the heart valve, that conforms to the shape of a dilated annulus. Thus, there is no need for forcing the heart valve to a remodelled shape when the support member is to be attached to the valve. This implies that the support member may be more easily attached to the valve, especially when operating on a beating heart. After the support member has been firmly attached to the valve, the shape change may be allowed such that the remodelling of the heart valve is performed.

Since the restraining member is biodegradable for removing the restraining action according to the first aspect of the invention, the support member may be firmly anchored to the valve tissue by overgrowth of endothelial cells while the restraining member is degraded. Thus, when the restraining member has been degraded to release the restrain on the support member, the support member will bring the valve tissue with it in assuming the desired course. Further, the surgeon may leave both the support member and the restraining member in the patient after implantation and the degradation will be performed by the immune system of the patient acting on the restraining member.

According to the second aspect of the invention, the change of shape of the support member may be actively controlled by providing a force to increase its cross-section. Thus, the support member may be fixed to the valve before a force is applied to increase the cross-section. The support member is suited to conform to the shape of at least a part of the valve annulus, but it will not unaffected increase its cross-section to assume the desired shape. This implies that the support member may be firmly anchored to the valve tissue before the support member is affected for assuming the desired shape. Thus, when an increase of the cross-section is created, the support member will bring the valve tissue with it in assuming the desired shape. As the support member shortens, the shape change of the support member may be designed such that valve tissue is drawn towards the opening in the valve in order for the valve to be remodelled for allowing the valve leaflets to close properly.

The support member may have an initial shape, when inserted to the heart valve, that conforms to the shape of a dilated annulus. Thus, there is no need for forcing the heart valve to a remodelled shape when the support member is to be attached to the valve. This implies that the support member may be more easily attached to the valve, especially when operating on a beating heart. After the support member has been firmly attached to the valve, the shape change may be allowed such that the remodelling of the heart valve is performed.

The cross-section of the support member may be increased at specific portions of the support member. The increase of the cross-section is directed to portions that are particularly suitable for treating the heart valve. The decision on which portions to be manipulated is based on the shape of the heart valve and the desired remodelling of the heart valve. Thus, the device allows control of the remodelling of the heart valve that is created by increasing the cross-section locally. However, the cross-section of the support member may alternatively be increased along the entire support member such that a general shortening of the support member is achieved for treating the heart valve symmetrically.

According to the third aspect of the invention, the change of shape of the support member may be actively controlled by controlling the temperature of the support member. Thus, the support member may be fixed to the valve while the support member is maintained in the first activated shape by keeping the temperature of the support member above said first temperature but below said second temperature. This implies that the support member may be firmly anchored to the valve tissue before the support member is heated for assuming the desired shape. Thus, when the support member is heated to assume its second activated shape, the support member will bring the valve tissue with it in assuming the desired shape. As the support member assumes its desired shape, the shape change of the support member may be designed such that valve tissue is drawn towards the opening in the valve in order for the valve to be remodelled for allowing the valve leaflets to close properly.

According to the fourth aspect of the invention, the restraining member is detachable from the support member for removing the restraining action. This implies that a surgeon may actively detach and withdraw the restraining member after the support member has been properly attached to the valve tissue.

The invention according to any of the four aspects contemplates various embodiments of the device, including embodiments for catheter-based surgery and embodiments for open heart surgery.

According to the first and fourth aspects of the invention, the support member may be arranged to be brought into the activated shape by receiving induced heating at selective portions of the support member. Thus, the support member may be inserted to a desired position in the inactivated shape and the shape of the support member during insertion is controlled both by the restraining member and the support member not striving towards assuming the desired course. By selectively heating the support member, selective portions of the support member may be brought to the activated shape and the heating controls what shape the support member will assume. The selective heating may be accomplished by a catheter with a heating element, which may be brought in contact with selective parts of the support member. The heating of the support member will initiate a strive of the support member to assume the activated shape. In order to facilitate placement and attachment of the support member to the heart valve, the support member may be firmly attached to the valve before the support member is heated.

According to all four aspects of the invention, the support member may be arranged to assume a reduced radius of curvature in the altered shape. This implies that the valve annulus may be remodelled such that it is moved inwards and the valve opening is decreased for ensuring that the valve leaflets close properly. However, other changes of the course of the support member may be contemplated for treating a diseased heart valve. For example, the course of the support member may be changed such that a radius of curvature is increased locally. Further, the course of the support member may be changed to introduce a depression or recess in the course of the support member. This implies that the support member, if applied on the atrial side of the heart valve, may push a leaflet towards the heart ventricle and, thereby, prevent a prolapsing leaflet from extending into the heart atrium.

According to the first aspect of the invention, the restraining member may be formed so as to control the rate of degradation in a patient. The restraining member may be arranged to degrade within a few weeks of implantation in a patient. This implies that the support members will be firmly attached to the valve by the time the restraining member is degraded. The degradation period of the restraining member may be controlled by the thickness and the material of the restraining member.

According to all four aspects of the invention, the support member may be a first support member and the device may further comprise a second support member at least partially formed from said shape memory material and connected to said first support member. The second support member is configured to abut an opposite side of the valve, whereby a portion of the valve tissue may be trapped between said first and second support members.

Such a device having a first and a second support member is applied to the heart valve in a much easier manner than conventionally utilized annuloplasty rings. The device may be rotated into place arranging the first and second support members on opposite sides of the heart valve. The support members trap valve tissue between them and thereby also at least partly attach the support members to the heart valve.

The first and second support members act to support valve tissue on opposite sides for e.g. aiding prolapsing leaflets to close properly. The first and second support members also act to remodel the valve, after the restraining action has been removed, in order to bring the leaflets closer to each other and thereby help the leaflets to close properly.

The shape of the second support member may be controlled in the same manner as the shape of the first support member. Thus, when a restraining action is removed or a desired shape of the support members is activated, both the first and the second support members may alter course for bringing valve tissue with them and remodel the heart valve. Alternatively, only one of the support members is restrained from assuming the desired course. However, this restrain may also prevent the other support member from fully assuming its desired course.

The first and second support members may be loop-shaped. As used herein, the term "loop-shaped" should be construed as a curved shape that may be closed as a ring with a circular, elliptic, or D-shaped form or any other closed form which may fit the shape of the valve annulus. The term "loop-shaped" also includes a curved shape that is open forming an arcuate shape, such as a C-shape or U-shape, which includes an angular turn of at least 180° such that the support member may abut valve tissue along a major part of the annular valve shape. The term "loop-shaped" also includes a curved shape that allows overlapping itself to form a portion of a coil.

The first loop-shaped support member may thus be continuous with the second loop-shaped support member to form a coil-shape. This facilitates rotating the support members into position on opposite sides of the heart valve. An end of the coil-shape may be brought to a commissure between leaflets of the heart valve and the coil-shape may be rotated such that the support members are placed on opposite sides of the valve.

The first and second support members may be D-shaped. Such shape would conform to the shape of the atrial valve annulus and is therefore especially useful for treatment of atrial valves.

At least the opposed surfaces of the first and second support members may be roughened, such as by the use of fabric, coatings, knurling or the like to facilitate better engagement and retention of the support members on the valve tissue. The opposed surfaces may be roughened in a pattern extending along the longitudinal direction of the loop-shape of the support members. This implies that the roughened surface will serve to prevent slippage of tissue through the pinch of the support members on opposite sides of the valve while presenting a low friction for the support members to be turned into position abutting the valve.

An outer boundary of the second support member may be greater than an outer boundary of the first support member. This implies that the device, when properly positioned at a heart valve, may be arranged such that the first and second support members are displaced to one another on the opposite sides of the heart valve. It has been found that this arrangement diminishes a risk that a rupture is created in the leaflets, which during normal heart action bends over the lower support member to open the valve. A possible explanation for this diminished rupture risk is that since the support members are displaced to one another, the pinch between the first and second support members does not sharply define a radial position in which the leaflets of the valve bend over the lower support member. When using the device on an atrial valve, the lower support member may now be arranged close to the annulus of the valve, which is larger on its ventricular side. Thereby, the device may also be arranged to minimally affect the movement of the leaflets during normal heart action. Further, a large lower support member provides a possibility to move the support member around the chords in the left ventricle during insertion of the device. However, it is conceivable that the diminished rupture risk may be achieved by instead making the outer boundary of the upper support member greater than the outer boundary of the lower support member.

According to the fourth aspect of the invention, the restraining member may be coil-shaped. This implies that the restraining member may be arranged to follow the shape at opposite sides of the heart valve for maintaining a large radius of curvature of the support members at both sides of the heart valve.

The first and second support members may be wound around the restraining member forming a helix having a global coil-shape. Thus, the restraining member forms an inner coil-shaped core inside a helix. This core will prevent the support members from assuming the desired radius. When the core is degraded, the support members are allowed to assume a coil-shape with a decreased radius.

Many other alternative embodiments of the restraining member are conceivable. For example, the restraining member may comprise one or more pins or bars extending between different positions on the support member and thus forcing these positions to be at a fixed distance to each other. According to another alternative, the support member is tubular and the restraining member is elongate and extendable through the tubular support member for exerting said restraining action. The restraining member may then be withdrawn from inside the tubular support member to release the restraining action.

According to the second aspect of the invention, the first and second support members may be tubular. Alternatively, the first and second support members may have a U-shaped cross-section. A support member presenting a tubular or U-shaped cross-section may be exposed to an outwardly pressing force such that the cross-section is increased in radial direction.

The first and second support members may be adapted to receive a balloon therein for expanding the cross-section of at least part of the support member. The balloon may suitably be used for insertion inside the support member and, upon inflation, provide an outwardly pressing force for increasing the cross-section.

As another alternative, the first and second support members may be belt-shaped. The cross-section of the belt may be increased by pulling the sides of the belt apart.

The first and second support members may be formed from a mesh-like structure. Such a structure may provide a possibility to alter the cross-section of the support member while changing the length of the support member. Suitably, the first and second support members may be stents.

According to a fifth aspect of the invention, there is provided a method for improving the function of a heart valve comprised of valve tissue including an annulus and a plurality of leaflets for allowing and preventing blood flow. The method comprises inserting an implantation device comprising a support member, wherein the implantation device is inserted such that the support member abuts one side of the valve. The support member is arranged along a first course conforming to the shape of at least part of the valve annulus. The method further comprises attaching the support member to valve tissue for fixating the position of the support member relative to the valve. The method further comprises activating a shape change of the support member such that the support member assumes a desired, altered course in order to remodel the heart valve.

According to the method, a device having an inherent possibility to change its shape is inserted into the heart valve of a patient. The device is properly attached to the heart valve conforming to the shape of at least part of the valve annulus before the shape change is activated. Thus, the method provides a possibility of allowing the support member to be firmly fixed to the valve tissue before the shape of change takes place and, therefore, the support member will bring the valve tissue with them in the change of shape for remodelling the heart valve. The method provides attaching a support member conforming to a shape of a dilated valve annulus before remodelling of the heart valve. This implies that the support member may be more easily attached to the valve, especially when operating on a beating heart.

According to one embodiment, the support member is at least partially formed from a shape memory material operable to assume an activated shape and an inactivated shape, and the implantation device further comprises a restraining member, which is arranged to provide a restraining action on a course of the support member. The insertion comprises bringing the shape memory material of the support member to an activated shape such that the support member is arranged along the first course while the restraining member exerts the restraining action on the support member. In this embodiment, the support member has an inherent strive to assume the desired course. However, the point of time of the shape change of the support member is controlled by means of the restraining member, such that the support member may be attached to the heart valve before it assumes the desired course.

In this embodiment, the activating comprises removing the restraining action of the restraining member allowing the support member to assume the desired, altered course.

The removing may comprise withdrawing the restraining member from the inserted implantation device. Thus, the restraining member may be arranged such that it may be withdrawn from the patient leaving the support member in position to assume the desired course.

Alternatively, the restraining member may be biodegradable and the removing may comprise leaving the support member and the restraining member in the patient in order for the restraining member to be degraded and remove the restraining action. This implies that the support member may be firmly anchored to the valve tissue by overgrowth of endothelial cells while the restraining member is degraded. Thus, when the restraining member has been degraded to release the restrain on the support member, the support member will bring the valve tissue with it in assuming the desired course.

According to another embodiment, the support member has an inherent adaptation to a shape change such that an increased cross-section of at least part of the support member is associated with a shortened length of the support member. The activating comprises expanding the cross-section of the support member such that the support member is shortened and assumes the desired, altered course. In this embodiment, the support member will not change shape until affected by a force for expanding a cross-section of the support member. Thus, the point of time of the shape change of the support member is controlled, such that the support member may be attached to the heart valve before it assumes the desired course.

The support member may be tubular or U-shaped and the expanding may comprise bringing a balloon in contact with at least part of the support member and inflating the balloon such that the cross-section of the support member is increased.

The support member may be a first support member and the implantation device may further comprise a second support member connected to the first support member. The insertion may further comprise placing said implantation device such that the second support member abuts an opposite side of the valve, the second support member being arranged along a first course conforming to the shape of at least part of the valve annulus at said opposite side.

The attaching may partly comprise placing the first and second support members in relation to each other on opposite sides of the heart valve such that a portion of the valve tissue is trapped between said first and second support members. The first and second support members may at least prevent the valve tissue from slipping through the pinch between the support members and altering the relation of the support members to the heart valve during fixation of the support members to the heart valve.

The activating may comprise activating a shape change of the second support member such that the second support member also assumes a desired, altered course in order to remodel the heart valve. This implies that the heart valve is treated from both sides and that the pinch of the valve tissue may be maintained after the support members have assumed the desired course.

The step of inserting may comprise inserting a first end of the first support member through a portion of the valve tissue, rotating the implantation device to position the first support member on a first side of the valve, and positioning the second support member on an opposite second side of the valve. The first and second support members are thus easily applied on opposite sides of the valve.

The step of inserting may further comprise introducing the implantation device into the patient inside a catheter. Thus, the implantation device may be introduced in a low invasive manner.

BRIEF DESCRIPTION OF THE DRAWINGS

The invention will now be described in further detail by way of example under reference to the accompanying drawings.

DETAILED DESCRIPTION OF THE INVENTION

Figure 1:
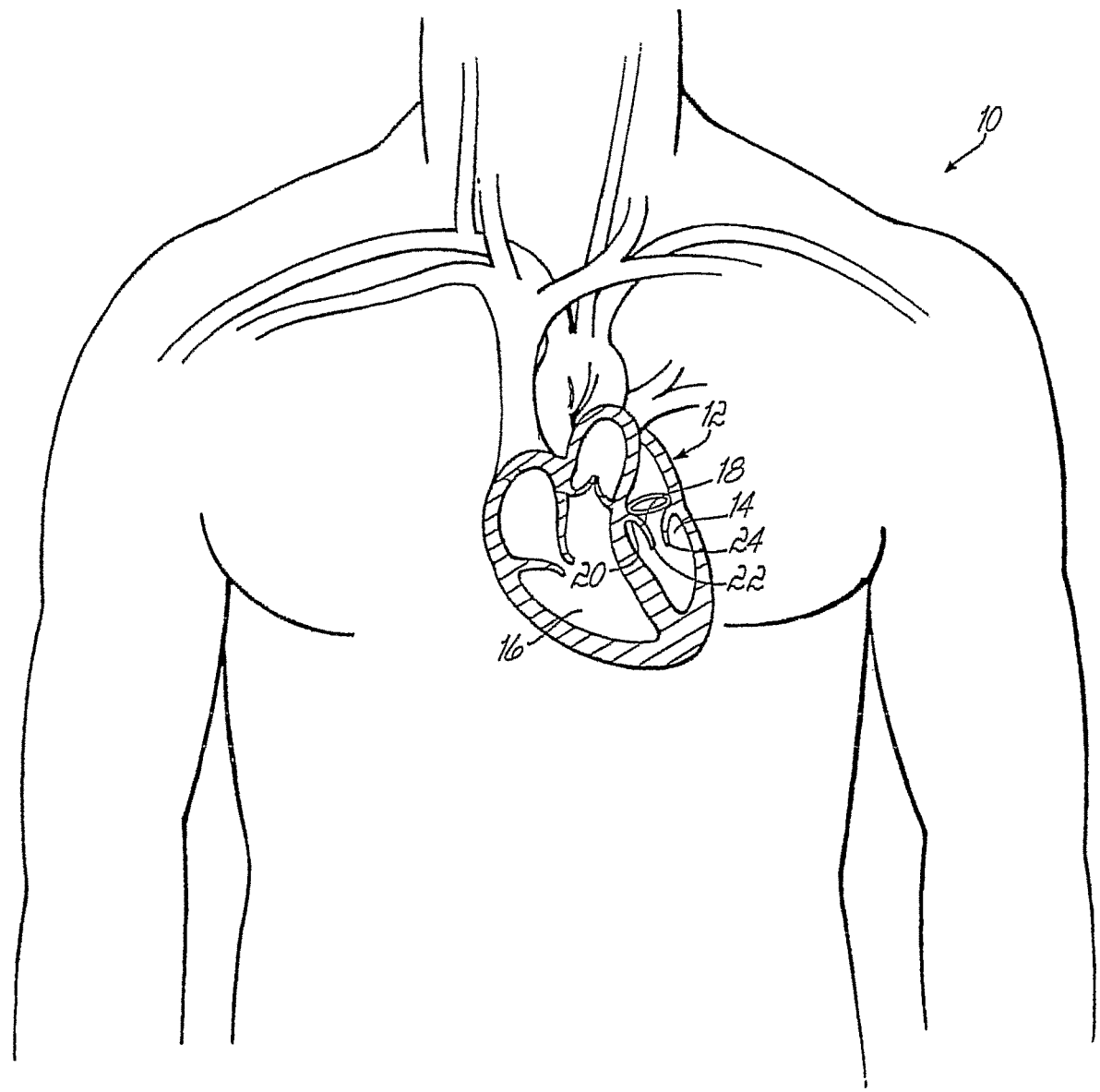
FIG. 1 schematically illustrates a patient with a heart shown in cross-section and a device of the present invention schematically illustrated as supporting the mitral valve.
Figure 1A:
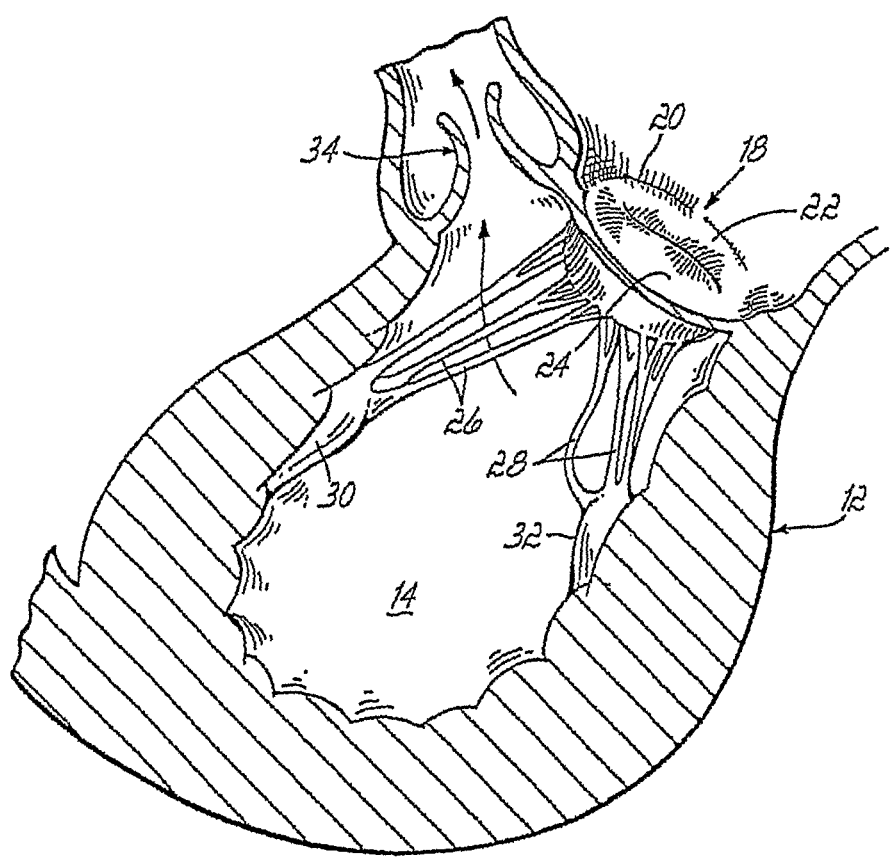
FIG. 1A is a cross-sectional view of the left ventricle showing the mitral valve in perspective.

FIG. 1 illustrates a patient 10 having a heart 12 shown in cross-section including a left ventricle 14 and a right ventricle 16. The concepts of the present invention are suitable to be applied, for example, to a mitral valve 18 which supplies blood into left ventricle 14. Mitral valve 18, as better shown in FIG. 1A, includes an annulus 20 and a pair of leaflets 22, 24 which selectively allow and prevent blood flow into left ventricle 14. It will be appreciated that the term valve tissue is used extensively throughout this disclosure in reference to the drawings. The inventive principles are equally applicable when referring to any valve tissue such as annulus tissue, leaflet tissue or other attached vessel tissue. Leaflets 22, 24 are supported for coaptation by chordae tendinae or chords 26, 28 extending upwardly from respective papillary muscles 30, 32. Blood enters left ventricle 14 through mitral valve 18 and is expelled during subsequent contraction of heart 12 through aortic valve 34. It will be appreciated that the present invention is applicable to tricuspidal heart valves as well.

Figure 2:
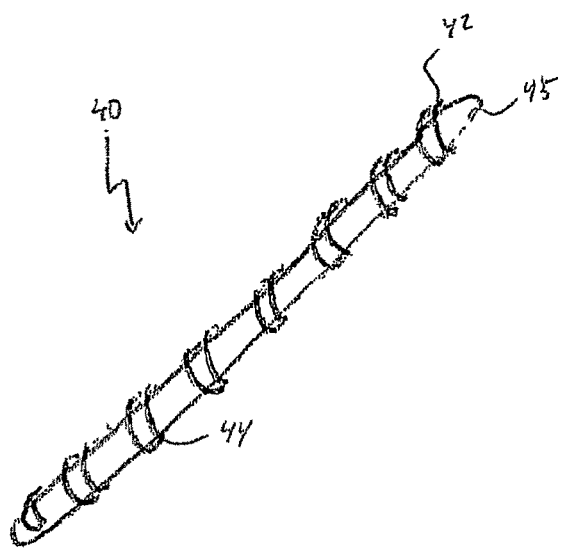
FIG. 2 is a perspective view of a device according to a first embodiment of the invention, wherein first and second support members of the device are shown in an inactivated shape suitable for insertion into a patient.
Figure 3:
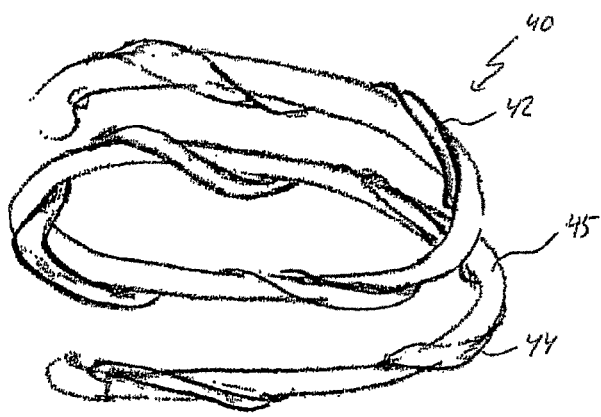
FIG. 3 is a perspective view of the device in FIG. 2, wherein the first and second support members have assumed an activated shape but are restrained by a restraining member.
Figure 4:
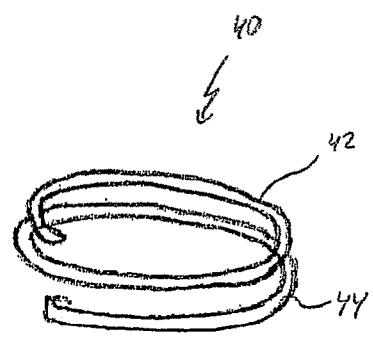
FIG. 4 is a perspective view of the device in FIG. 2, wherein the first and second support members have assumed a desired, activated shape after release of the restrain from the restraining member.

A device 40 according to a first embodiment of the present invention is shown in FIGS. 2-4. The device comprises a first and a second support member 42, 44. The first support member 42 is continuous with the second support member 44. The first and second support members 42, 44 are formed from a shape memory material, such as alloys based on e.g. Nitinol, copper-zinc-aluminium, or copper-aluminium-nickel, or a shape memory polymer, which may be polynorborene-, polyisoprene-, styrene butadiene-, and polyurethane-based materials and vinyl acetate- and polyester-based compounds.

The first and second support members 42, 44 have an inactivated shape and an activated shape. In the inactivated shape, the support members 42, 44 are flexible and may be easily deformed. In the activated shape, the support members 42, 44 have a strong strive towards assuming a desired, preprogrammed shape. The support members 42, 44 may enter an activated shape by being exposed to a temperature above a transition temperature. Thus, the device 40 may be inserted in a low invasive manner, the support member 42, 44 being in the inactivated shape. The device 40 may then assume the desired shape when placed in the proper position in the patient by the support members 42, 44 being brought to their activated shape. The support members 42, 44 may be arranged to be brought into the activated shape by receiving induced heating at selective portions of the support members 42, 44. By selectively heating the support members 42, 44, selective portions of the support members 42, 44 may be brought to the activated shape and the heating controls what shape the support members 42, 44 will assume. The selective heating may be accomplished by a catheter with a heating element, which may be brought in contact with selective parts of the support members 42, 44.

The device 40 further comprises a restraining member 45. The restraining member 45 is arranged to prevent the support members 42, 44 from fully assuming the desired activated shape. The restraining member 45 is coil-shaped and is formed from a biodegradable material, such as a material based on polyglycolic acid, copolymers of glycolic acid and lactic acid, or various lactide polymers. The biodegradable material will be degraded or resorbed when implanted in a patient. The time period for degradation will depend on the particular material and the thickness of the restraining member 45. Thus, this may be controlled by the design of the restraining member 45.

As shown in FIGS. 2-3, the first and second support members 42, 44 may be wound around the restraining member 45. This allows the restraining member 45 to restrain the support members 42, 44 from assuming the preprogrammed shape. As shown in FIG. 2, the device 40 may be arranged in a generally elongate shape in the inactivated shape of the support members 42, 44. This elongate shape is suitable for placing the device 40 inside a catheter for insertion into a patient. The coil-shaped restraining member 45 is thus stretched out for allowing it to be placed inside a catheter.

In FIG. 3, the device 40 is shown with the support members 42, 44 being in an activated shape. The restraining member 45 has assumed its coil-shape and prevents the support members 42, 44 from fully obtaining the activated shape. The restraining member 45 forces the support members 42, 44 to follow a coil-shape having a larger radius of curvature than the preprogrammed shape.

When implanted in a patient, the restraining member 45 will be degraded. In FIG. 4, the device 40 is shown after the restraining member 45 has been degraded and the first and second support members have fully assumed the activated, preprogrammed shape. The first and second support members 42, 44 now form a general coiled configuration in the form of a spiral or key ring-type configuration with two loops.

Alternatively, the restraining member 45 may be withdrawn during implantation of the device 40 in a patient. Thus, the restraining member 45 may be withdrawn when the first and second support members 42, 44 have been properly placed allowing the support members 42, 44 to fully assume the activated shape. This implies that a surgeon may see the result of the full shape change of the support members 42, 44 during implantation of the device 40 and may directly get an indication of the success of the surgery.

As a further alternative, the restraining member may be implemented as one or more bars extending between different positions on the first and second support members 42, 44. These bars may thus keep the positions on the support members 42, 44 at a fixed distance to each other and, in this way, prevent the support members 42, 44 to fully assume the activated shape. The bars may be formed from a biodegradable material as described above. Alternatively, the bars may be detached from the support members 42, 44 and removed during implantation, or the bars may be cut during implantation in order to remove the restraining action of the bars.

Figure 5:
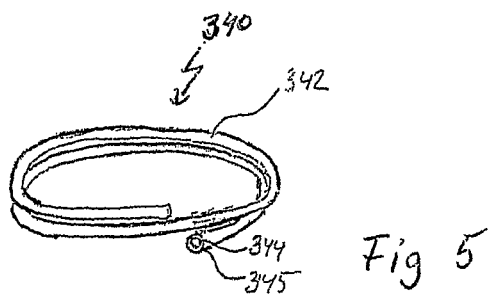
FIG. 5 is a perspective view of an alternative device according to the first embodiment of the invention.
Figure 6:
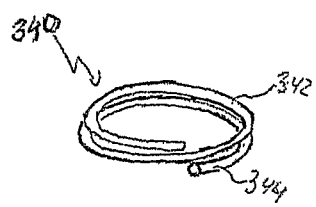
FIG. 6 is a perspective view of the device of FIG. 5 having assumed a desired, activated shape.

According to an alternative shown in FIGS. 5-6, a device 340 comprises a first and a second support member 342, 344. The first support member 342 is continuous with the second support member 344. The first and second support members 342, 344 are formed from a shape memory material. The first and second support members 342, 344 are coated with a biodegradable sheath 345. During manufacture of the device 340, the first and second support members 342, 344 may be immersed in a biodegradable material being in a liquid state. The first and second support members 342, 344 may be immersed into the biodegradable material in an inactivated, flexible state, while being held in a coil-shape that may fit for placing the device within a heart such that the first and second support members may conform to the shape of at least a part of the valve annulus at opposite sides of the valve. The first and second support members 342, 344 may thus be embedded in a biodegradable sheath 345. When the biodegradable sheath 345 is degraded within a patient, the first and second support members 342, 344 are allowed to assume the activated shape, wherein a reduced radius of the coil-shape is obtained as illustrated in FIG. 6.

Figure 7:
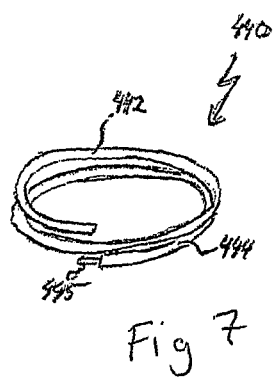
FIG. 7 is a perspective view of yet another alternative device according to the first embodiment of the invention.
Figure 8:
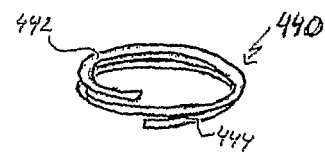
FIG. 8 is a perspective view of the device of FIG. 8 having assumed a desired, activated shape.

According to yet another alternative illustrated in FIGS. 7-8, a device 440 comprises a first and a second support member 442, 444. The first support member 442 is continuous with the second support member 444. The first and second support members 442, 444 are formed from a shape memory material. The first and second support members 442, 444 are tubular. The device 440 further comprises an elongate restraining member 445 that may be arranged extending within the tubular first and second support members 442, 444. The restraining member 445 may be pushed to extend through the entire first and second support members 442, 444 in order to force the first and second support members 442, 444 to a coil-shape with a large radius. By withdrawing the restraining member 445 from inside the support members 442, 444, the support members 442, 444 are allowed to assume an activated shape wherein the coil-shape has a decreased radius as illustrated in FIG. 8.

The second support member 44 has an outer boundary which is greater than the outer boundary of the first support member 42. The support members 42, 44 have corresponding shapes with the second support member 44 being in larger scale than the first support member 42. This is advantageous in creating a pinch of the valve tissue between the first and second support members 42, 44, as will be described below with reference to FIG. 14. An end of the second support member 44 and the corresponding end of the restraining member 45, which will lead the coil during insertion of the device 40 at the valve, has a greater pitch than the rest of the coil. This implies that the leading end of the coil during rotation into position in the valve will project from immediate contact with the valve tissue and, therefore, the risk that the coil is caught by the chords is diminished.

Figure 9:
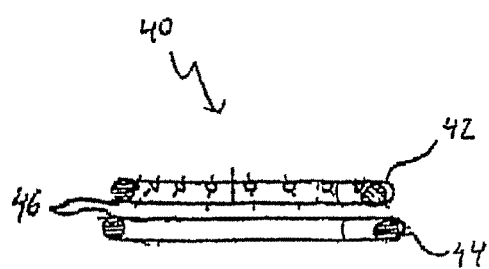
FIG. 9 is a cross-sectional view of the device in FIG. 4.

The device 40 is shown in cross-section in FIG. 9. The first and second support members 42, 44 have a round cross-sectional shape. Opposed surfaces 46 of the first and second support members 42, 44 provide a pinch to trap valve tissue therebetween. The round cross-section is also advantageous in creating a pinch of the valve tissue which will not harm the leaflets in their movement during normal heart action, as will be further described below with reference to FIG. 21.

Figure 10:
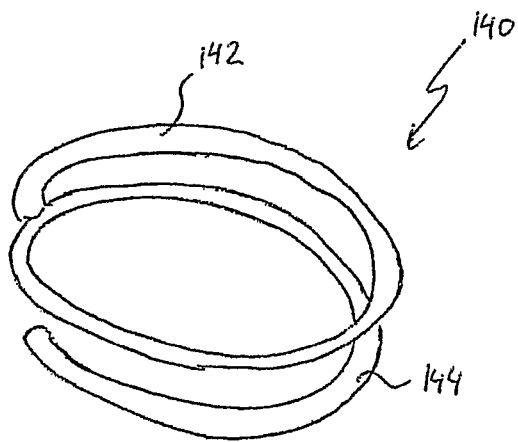
FIG. 10 is a perspective view of a device according to a second embodiment of the invention, wherein first and second support members of the device are shown in a first shape having a small cross-section.
Figure 11:
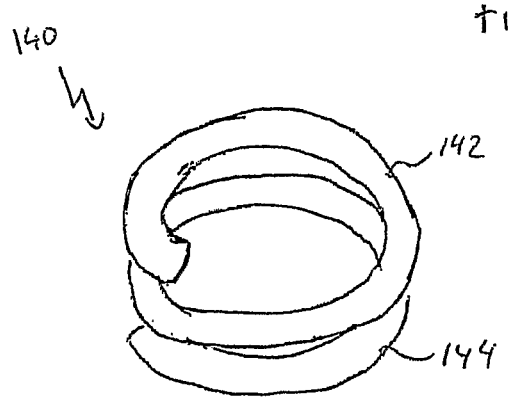
FIG. 11 is a perspective view of the device in FIG. 10, wherein the cross-section has been increased and the first and second support members have assumed an altered shape.

A device 140 according to a second embodiment of the present invention is shown in FIGS. 10-12. The device 140 comprises a first and a second support member 142, 144. The first support member 142 is continuous with the second support member 144. The first and second support members 142, 144 are formed from a mesh-type or netlike structure, such as stents.

The first and second support members 142, 144 have an inherent adaptation to a shape change such that an increased cross-section of at least part of the support member 142, 144 is associated with a shortened length of the support member 142, 144. This foreshortening is accomplished in that the mesh-type structure, when expanded in cross-section, pulls the ends of the support members 142, 144 towards each other.

The support members 142, 144 present a shape change that may be controlled. The shape change will not occur until a force is applied for increasing the cross-section of at least part of the first and second support members 142, 144. This implies that the second embodiment as well as the first embodiment provides a possibility to place a device in relation to a heart valve and, thereafter, control the point of time when the device placed at the heart valve is going to perform a change of shape.

In FIG. 10, the device 140 is shown with the support members 142, 144 arranged in a first shape suitable for being attached to the heart valve. In this first shape the support members 142, 144 conform to the shape of the heart valve annulus, such that the support members 142, 144 may be attached to the annulus along the entire course of the support members 142, 144. The first and second support members 142, 144 form a general coiled configuration in the form of a spiral or key ring-type configuration with two loops, such that the support members 142, 144 may abut opposite sides of a heart valve.

In FIG. 11, the device 140 is shown after the support members 142, 144 have been exposed to a force increasing the cross-section of the support members 142, 144. The increased cross-section has forced the support members 142, 144 to shorten. The first and second support members 142, 144 now form a coiled configuration having a decreased radius of curvature to accommodate to the shortened length of the support members 142, 144.

Figure 12A:
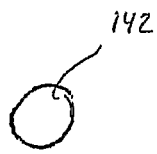
FIGS. 12a-c are cross-sectional views of the device according to the second embodiment.
Figure 12B:
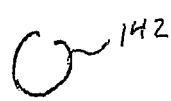
Figure 12C:

In FIGS. 12a-c, different cross-sections of the first and second support members 142, 144 are illustrated. In FIG. 12a, the support members 142, 144 are tubular having a circular cross-section. In FIG. 12b, the support members 142, 144 have a U-shaped cross-section. Both these cross-sections are suitable for receiving an inflatable balloon inside the cross-sectional structure. Inflation of the balloon will thus force the cross-section to increase radially. In FIG. 12c, the support members 142, 144 are belt-shaped having a linear cross-section. This cross-section may be increased by pulling the edges of the belt apart.

Figure 13:
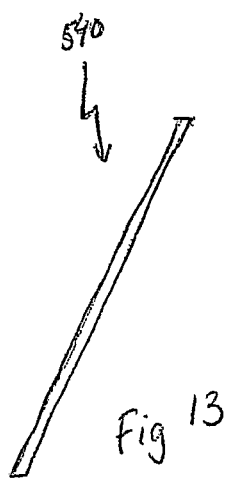
FIG. 13 is a perspective view of a device according to a third embodiment of the invention, wherein the device is in an inactivated shape.
Figure 14:
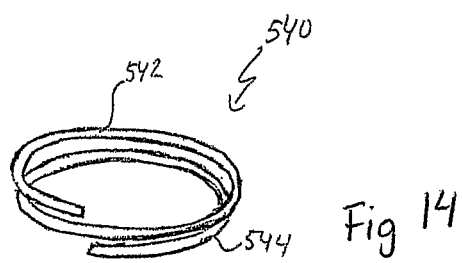
FIG. 14 is a perspective view of the device in FIG. 13, wherein the device is in a first activated shape.
Figure 15:
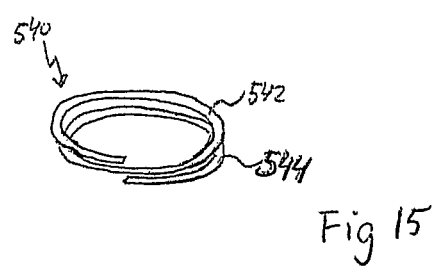
FIG. 15 is a perspective view of the device in FIG. 13, wherein the device is in a second activated shape.

A device 540 according to a third embodiment is shown in FIGS. 13-15. The device 540 comprises a first and a second support member 542, 544. The first support member 542 is continuous with the second support member 544. The first and second support members 542, 544 are formed from a shape memory material. The shape memory material is treated to form a first and a second activated shape. The first and second support members 542, 544 may thus assume two different shapes depending on the temperature of the device 540. In an inactivated shape as illustrated in FIG. 13, the device 540 is flexible and may be arranged in an elongate form in order to facilitate introduction of the device to a heart of a patient via a catheter. The device 540 may be cooled during introduction in the catheter in order to maintain its inactivated shape. The device 540 may then be heated to a first temperature by utilizing the body temperature. Then, the device 540 is brought to the first activated shape as illustrated in FIG. 14 forming a coil-shape with a large radius suitable for placing the first and second support members 542, 544 in contact with opposite sides of a heart valve and fixing the position of the support members 542, 544 to the valve annulus. The device 540 may further be heated to a second temperature by further utilizing the body temperature. Then, the device is brought to the second activated shape as illustrated in FIG. 15. The device 540 in the second activated shape forms a coil-shape with a smaller radius suitable for diminishing a radius of the valve annulus.

Figure 16:
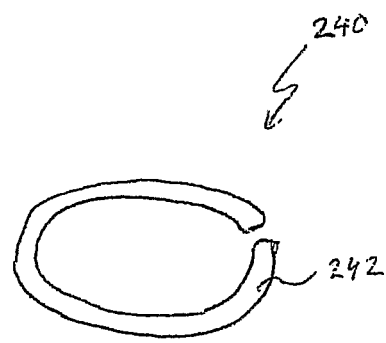
FIG. 16 is a perspective view of a device according to a fourth embodiment of the invention, wherein the device comprises only one support member.
Figure 17:
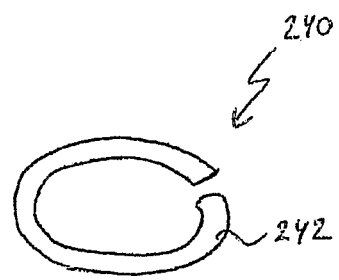
FIG. 17 is a perspective view of the device in FIG. 16, wherein the device has assumed an altered shape.

A device 240 according to a fourth embodiment of the present invention is shown in FIGS. 16-17. The device 240 comprises only one support member 242. The support member 242 is arranged to be placed only on one side of a heart valve.

The support member 242 may be formed from a shape memory material having an inactivated shape and an activated shape. In the inactivated shape, the support member 242 is flexible and may be easily deformed. In the activated shape, the support member 242 has a strong strive towards assuming a desired, preprogrammed shape. The device 240 may be inserted in a low invasive manner, the support member 242 being in the inactivated shape. The device 240 may then assume the desired shape when placed in the proper position in the patient by the support member 242 being brought to their activated shape. The device 240 may further comprise a restraining member (not shown), which is arranged to prevent the support member 242 from fully assuming the desired activated shape. The restraining member may thus control the point of time when the support member 242 is fully brought to its desired activated shape. The support member 242 may be wound around the restraining member or the restraining member may extend between two positions on the support member fixating the distance between these positions.

The support member 242 may alternatively be formed from a mesh-type or netlike structure having an inherent adaptation to a shape change such that an increased cross-section of at least part of the support member 242 is associated with a shortened length of the support member 242. The support member 242 presents a shape change that may be controlled. The shape change will not occur until a force is applied for increasing the cross-section of at least part of the support member 242.

According to a further alternative, the support member 240 may be formed from a shape memory material treated to form a first and a second activated shape.

In FIG. 16, the device 240 is shown with the support member 242 being in a first shape conforming to the shape of the annulus of the heart valve to be treated.

In FIG. 17, the device 240 is shown after the support member 242 has been allowed to perform a change of shape to assume the desired shape. Either a restraining action of a restraining member has been removed or a cross-section of the support member 242 has been increased in order to activate the shape change. The support member 242 has now changed shape to decrease a radius of curvature for remodelling the heart valve and decreasing the size of the heart valve annulus.

Referring now to FIGS. 18-22, a method for repairing a heart valve by means of the device according to the first embodiment will be described. The concept of this method may be applied to the device according to the second, third or fourth embodiments as well, as would be understood by a person skilled in the art. As been described above, the shape change of the device may be activated in different ways, depending on the embodiment of the device. However, the point of time when the shape change is activated may be controlled irrespective of which embodiment is used. Thus, it may be ascertained that the device is firmly attached to the heart valve before the shape change occurs, such that the heart valve may be properly remodelled as will be described below.

Figure 18A:
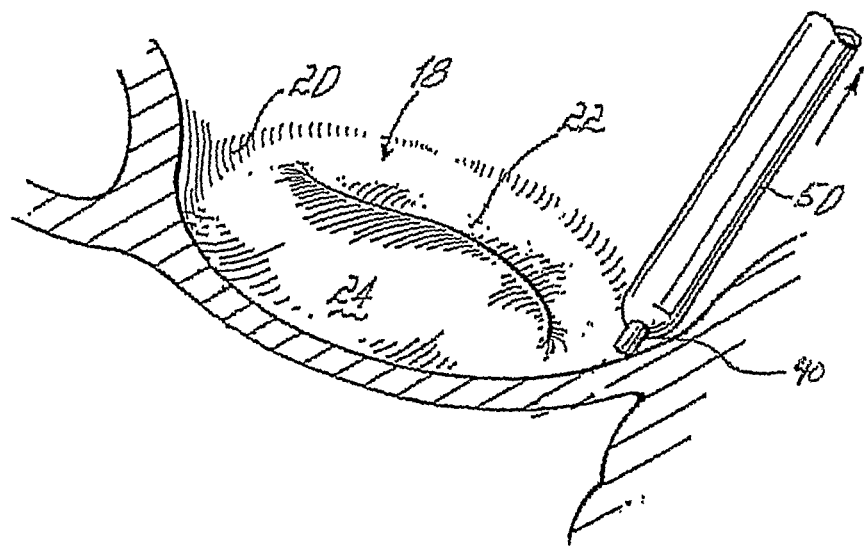
FIGS. 18a-b are partially sectioned perspective views of the mitral valve and the device according to the first embodiment of the invention during implantation of the device.
Figure 18B:
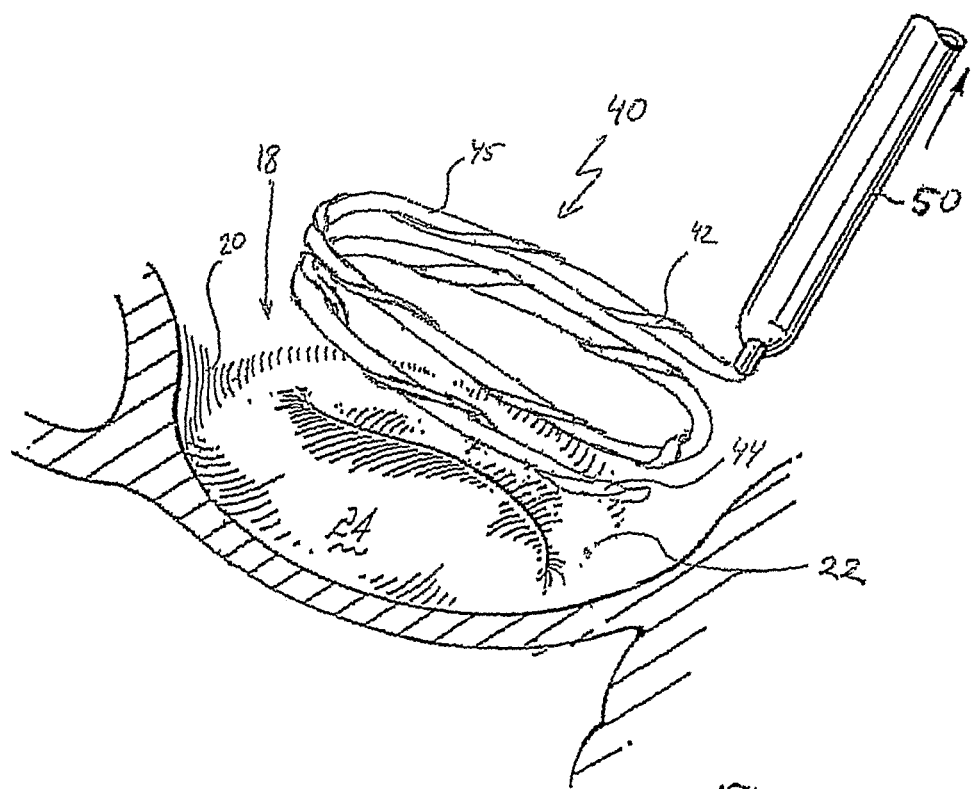

First, access to the heart valve is achieved by means of conventional catheter techniques, including making puncture in a vessel and guiding the catheter through the vascular system into the heart. In FIG. 18a, the device 40 is shown when being inserted to the mitral valve 18. The device 40 is being carried in a catheter 50, which extends from the outside of the patient into the heart. The device 40 may be pushed out of the catheter 50 using a gripping tool (not shown) extending through the catheter 50. When pushed out of the catheter 50, the restraining member 45 assumes its coil-shape. An end of the restraining member and the second support member 44 is brought to the opening of the mitral valve 18 at a commissure between the leaflets 22, 24, as shown in FIG. 18b. The end is led through the opening and the device 40 is turned 360 degrees. Thus, the second support member 44 will be rotated into place on one side of the valve 18, whereas the first support member 42 is placed on the opposite side of the valve 18.

Figure 19:
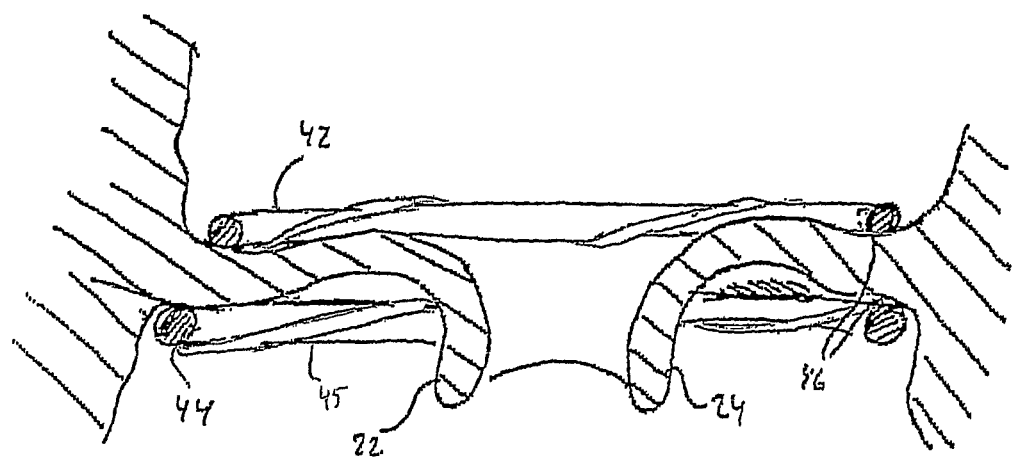
FIG. 19 is a partially sectioned perspective view showing the device of the invention after having been turned into position.

The first and second support members 42, 44 are now brought to their activated shape by e.g. heating them above a transition temperature. The heating may be provided by the body temperature of the patient or by means of heating energy being transmitted through a conductor (not shown) in the catheter. This implies that the first and second support members 42, 44 strive towards assuming the preprogrammed shape. The first and second support members 42, 44 on opposite sides of the valve will now be drawn towards each other for securely trapping valve tissue therebetween. The restraining member 45 will prevent the first and second support members 42, 44 from fully assuming the activated shape and, thus, from reducing the radius of curvature of the coil-shape. In this way, the device 40 is arranged in engagement with the valve 18, as shown in FIG. 19.

The support members 42, 44 are now placed on opposite sides of the valve 18 pinching valve tissue therebetween to maintain a shape of the valve 18. The support members 42, 44 may have roughened, opposed surfaces 46 to better keep the leaflets 22, 24 from slipping through the pinch. This implies that the position of the support members 42, 44 relative the heart valve is initially fixed.

Figure 20A:
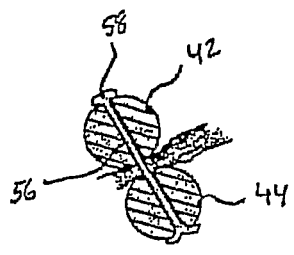
FIGS. 20a-b are cross-sectional views illustrating fixation of the device to the heart valve.
Figure 20B:
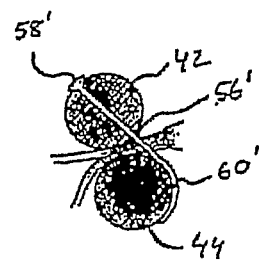

The device 40 may now be secured to the valve 18 for strengthening the fixation of the relative position between the support members 42, 44 and the valve tissue. The support members 42, 44 may comprise respective bores 54 through the opposed support members for receiving separate fasteners 56. The fasteners 56 may be threaded or unthreaded pins and may be pushed into position extending through bores in both support members and valve tissue therebetween. The fastener may have an end 58 with larger diameter than the bores 54 such that the fastener 56 may not fall through the bore 54. In this way, the device 40 is firmly attached to the valve 18 for keeping the valve annulus 20 in its reshaped form, as illustrated in FIG. 20a. Many alternative embodiments of the fasteners may be contemplated. As shown in FIG. 20a, the fasteners 56 may have an end 60 with an expandable diameter for securing the fastener 56 after it has been pushed through the bores 54. Alternatively, the fastener 56' may have a curved portion 60' for gripping around one of the support members, such that the fastener 56' may extend through a bore 54 in one support member and around the other support member, as illustrated in FIG. 20b. As further alternatives, the fasteners may be clips, sutures, or projections that are extendable from at least one of the support members for engaging the valve tissue.

Figure 21:
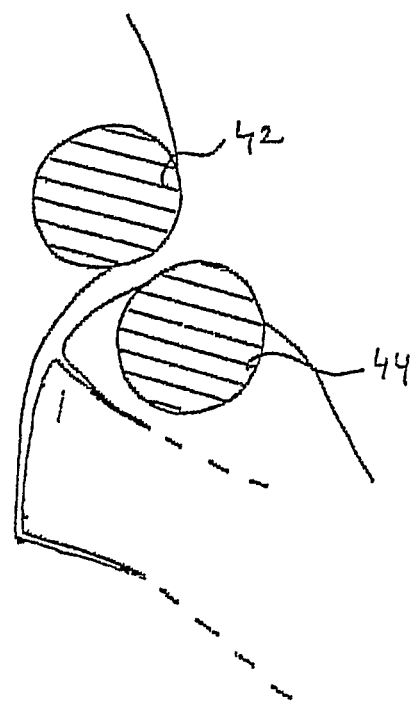
FIG. 21 is a cross-sectional view of the implanted device in FIG. 18.

As illustrated in FIG. 21, the second support member 44 is slightly displaced radially with respect to the first support member 42. This implies that the first and second support members 42, 44 are not arranged directly on top of each other. The pinch between the first and second support members is therefore not sharply defined in a radial direction of the valve. This implies that a pinching force between the support members is not focussed to a specific radial position of the valve. As a result, the pinching force does not affect the movement of the leaflets during normal heart action and there is a diminished risk of rupture in the leaflets at the pinch. The support members are interrelated in such manner that the outer boundary of the first support member 42 has a diameter corresponding to a line through the center of the second support member 44. Thus, the support members 42, 44 overlap somewhat such that tissue is not allowed to move through the pinch and the shape of the valve is maintained. Further, the cross-section of the support members 42, 44 is round, which also gives a soft contact between the support members and the valve tissue to further diminish the risk of rupture in the leaflets.

Figure 22:
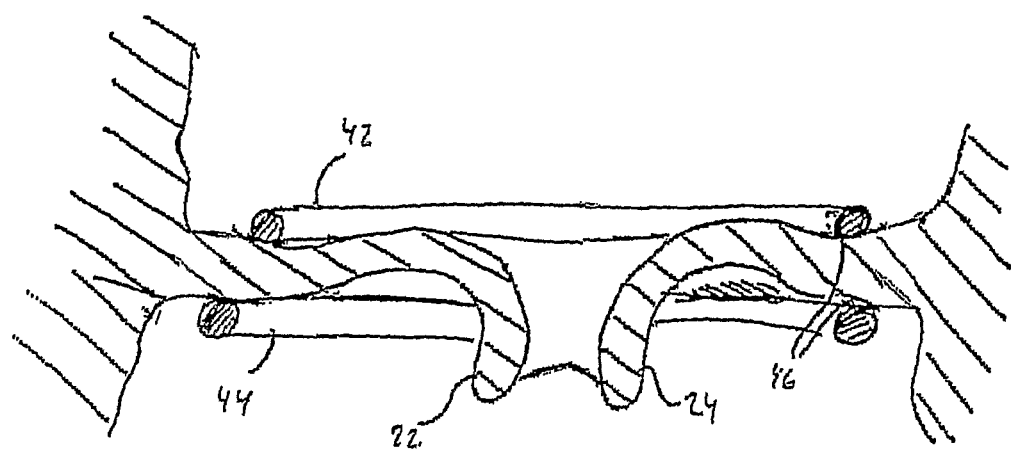
FIG. 22 is a perspective view showing the implanted device after the restraining member has been degraded.

After the device 40 has been placed at the heart valve forming a pinch of the valve tissue, the catheter 50 will be retracted and the device 40 is left in the patient. The restraining member 45 will be degraded in the patient during a time period of a few weeks. During this time, the support members 42, 44 will grow into the valve tissue for further securing the support members 42, 44 to the valve. When the restraining member 45 has been degraded, the support members 42, 44 are able to fully assume the activated shape. Thus, the support members 42, 44 will reduce the radius of curvature of the coil-shape and bring the pinched valve tissue in the shape change so as to remodel the valve, as illustrated in FIG. 22. The leaflets 22, 24 are thus brought closer together for ensuring that they may close the valve properly.

It should be emphasized that the preferred embodiments described herein are in no way limiting and that many alternative embodiments are possible within the scope of protection defined by the appended claims.

For example, the access to the heart valve may be achieved endoscopically or with open heart surgery. In such case, the device 40 may have a coil-shape already during insertion into the heart.

Many different shapes may be contemplated for the loop-shaped support members. For example, the support members may have elliptical, circular or D-shaped forms. One or both support members need not make an angular turn of 360° such as to have a C or U-shape instead.

Further, different shape changes may be contemplated. The course of the support member may be changed such that a radius of curvature is increased locally. Further, the course of the support member may be changed to introduce a depression or recess in the course of the support member.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for improving the function of a heart valve comprising:
    obtaining a support member at least partially formed from a shape memory material,
    inserting a first segment of the support member to abut a first side of the heart valve,
    inserting a second segment of the support member to abut a second side of the heart valve, opposite the first side,
    heating the shape memory material to a first temperature to bring the support member to a first activated shape where the first segment forms a coil shape with the second segment and conforms to the heart valve annulus,
    after the support member has achieved the first activated shape, fixing the support member to the annulus of the heart valve while the support member is maintained in the first activated shape by keeping the temperature of the support member above the first temperature but below a second temperature,
    heating the shape memory material to the second temperature to bring the shape memory material to assume a second activated shape upon which the support member assumes an altered shape to remodel the heart valve annulus,
    wherein the support member is arranged to assume a reduced radius of curvature in the altered shape.

2. Method according to claim 1, wherein the support member is loop-shaped.

3. Method according to claim 1, wherein a portion of the tissue of the heart valve is trapped between the first and second support members.

4. Method according to claim 3, wherein the second segment is configured to assume an altered shape for remodeling the heart valve annulus upon the shape memory assuming the second activated shape.

5. Method according to claim 3, wherein the second segment is loop-shaped.

6. Method according to claim 3, wherein an outer boundary of the second segment is greater than an outer boundary of the first segment.

7. Method according to claim 1, wherein heating the support member comprises inducing heating at selective portions of the support member to bring the selective portions to the altered shape.

8. Method according to claim 7, comprising bringing a heating element of a catheter in contact with the selective portions.

9. Method according to claim 1, comprising introducing the support member into the heart upon the support member assuming an inactivated, elongate shape in a catheter.

10. Method according to claim 9, comprising cooling the support member in the catheter to maintain the inactivated, elongate shape.

11. A method for improving the function of a heart valve comprising:
    obtaining a support member at least partially formed from a shape memory material,
    inserting a first segment of the support member to abut a first side of the heart valve,
    inserting a second segment of the support member to abut a second side of the heart valve, opposite the first side,
    heating the shape memory material to a first transition temperature to cause the support member to change shape to a first activated shape where the first segment forms a coil shape with the second segment and conforms to the heart valve annulus,
    after the support member has achieved the first activated shape, fixing the support member to the annulus of the heart valve while the support member is maintained in the first activated shape by keeping the temperature of the support member above the first transition temperature but below a second transition temperature,
    heating the shape memory material to the second transition temperature to cause the shape memory material to change shape to a second activated shape upon which the support member assumes an altered shape to remodel the heart valve annulus,
    wherein the support member is arranged to assume a reduced radius of curvature in the altered shape.

* * * * *